(12) United States Patent
Hazama

(10) Patent No.: US 10,575,859 B2
(45) Date of Patent: Mar. 3, 2020

(54) HEMOSTATIC DEVICE

(71) Applicant: TERUMO KABUSHIKI KAISHA, Shibuya-ku, Tokyo (JP)

(72) Inventor: Kenichi Hazama, Bear, DE (US)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 253 days.

(21) Appl. No.: 15/643,096

(22) Filed: Jul. 6, 2017

(65) Prior Publication Data

US 2018/0008283 A1 Jan. 11, 2018

(30) Foreign Application Priority Data

Jul. 6, 2016 (JP) .................. 2016-134608

(51) Int. Cl.
*A61B 17/135* (2006.01)
*A61B 17/132* (2006.01)

(52) U.S. Cl.
CPC ........ *A61B 17/135* (2013.01); *A61B 17/1325* (2013.01)

(58) Field of Classification Search
CPC ......... A61B 17/132–1355; A61B 2013/00468; A61B 5/02–0295; A61B 25/10–2025/1097; A61B 5/022; A61F 2013/00468
See application file for complete search history.

(56) References Cited

U.S. PATENT DOCUMENTS

| | | | |
|---|---|---|---|
| 5,799,650 A * | 9/1998 | Harris | A61B 17/1325 128/107.1 |
| 6,752,820 B1* | 6/2004 | Hafemann | A61B 17/1325 606/203 |
| 7,498,477 B2 | 3/2009 | Wada et al. | |
| 8,481,803 B2 | 7/2013 | Wada et al. | |
| 8,524,974 B2 | 9/2013 | Wada et al. | |
| 8,759,603 B2 | 6/2014 | Wada et al. | |
| 2004/0098035 A1* | 5/2004 | Wada | A61B 17/1325 606/201 |
| 2008/0183292 A1* | 7/2008 | Trieu | A61F 2/441 623/17.11 |
| 2015/0018869 A1* | 1/2015 | Benz | A61B 17/135 606/203 |

(Continued)

FOREIGN PATENT DOCUMENTS

JP 2004-201829 A 7/2004

*Primary Examiner* — Katrina M Stransky
*Assistant Examiner* — Brigid K Byrd
(74) *Attorney, Agent, or Firm* — Buchanan Ingersoll & Rooney PC (57) ABSTRACT

A hemostatic device includes a band for being wrapped around a wrist W, securing means for securing the band in a state where the band is wrapped around the wrist, and an inflation portion disposed on an inner peripheral surface of the band, and that is inflated by injecting gas. The inflation portion has a first layer and a second layer which covers an outer surface of the first layer. The first layer is formed of a material which has a larger gas permeation amount per unit area than a material for forming the second layer. The second layer has gap portions which can expose the outer surface of the first layer outward from the second layer in a state where the inflation portion is inflated.

16 Claims, 9 Drawing Sheets

(56) References Cited

U.S. PATENT DOCUMENTS

2015/0327870 A1* 11/2015 Fortson ................ A61B 17/135
  606/202
2015/0327871 A1* 11/2015 Fortson ................ A61B 17/135
  606/202
2016/0338709 A1   11/2016 Wada et al.

* cited by examiner

HEMOSTATIC DEVICE

CROSS-REFERENCE TO RELATED APPLICATION

This application claims priority to Japanese application number 2016-134608 filed on Jul. 6, 2016, the entire content of which is incorporated herein by reference.

TECHNICAL FIELD

The disclosure herein relates to a hemostatic device used for performing hemostasis by compressing a punctured site.

BACKGROUND ART

In recent years, percutaneous treatment and examination have been performed in which a blood vessel in the arms or legs is punctured and an introducer sheath is introduced into a puncture site so as to deliver a medical device such as a catheter to a lesion area via a lumen of the introducer sheath. In a case where these treatments and examinations are performed, an operator needs to perform hemostasis at the puncture site after the introducer sheath is removed therefrom. In order to perform hemostasis, a known hemostatic device is used which includes a band for being wrapped around a limb such as the arms and legs, securing means for securing the band in a state where the band is wrapped around the limb, and an inflation portion that interlocks with the band, and that is inflated by injecting a fluid so as to compress the puncture site.

According to such a hemostatic device, if the inflated inflation portion continues to strongly compress the puncture site and a blood vessel or a nerve around the puncture site for a long time, there is a possibility that numbness or pain may be caused or the blood vessel may be occluded. In order to prevent the vascular occlusion, a physician or a nurse generally inflates the inflation portion. Thereafter, he or she periodically connects a dedicated instrument such as a syringe to the hemostatic device, discharges a fluid contained inside the inflation portion, and performs a decompressing operation for reducing internal pressure of the inflation portion, thereby reducing the compressing force acting on the puncture site with the lapse of time.

In contrast, according to the hemostatic device disclosed in JP-A-2004-201829, the inflation portion is configured to include a material which stretches with the lapse of time. Therefore, after the inflation portion is inflated by injecting the fluid into the inflation portion, the inflation portion is gradually inflated and deformed by pressure applied from the fluid inside the inflation portion. Whereas the amount of the fluid inside the inflation portion does not substantially decrease, the volume of an internal space of the inflation portion gradually increases. Accordingly, the internal pressure of the inflation portion can be reduced with the lapse of time. In this manner, the compressing force acting on the puncture site can be reduced with the lapse of time.

According to the hemostatic device disclosed in JP-A-2004-201829, the physician or the nurse can save time and effort when performing the decompressing operation. However, if the inflation portion is configured to include the material which stretches with the lapse of time, the inflation portion is progressively inflated and deformed with the lapse of time. As a result, a thickness of the inflation portion becomes thinner. From a viewpoint of satisfactorily maintaining strength of the inflation portion, it is conceivable that the thickness of the inflation portion is preferably maintained to some extent.

SUMMARY

The disclosure herein is directed to a hemostatic device which can satisfactorily maintain strength of an inflation portion, which does not need to be operated by a physician or a nurse, and which can reduce a compressing force acting on a hemostasis-requiring site with the lapse of time to such an extent that vascular occlusion can be prevented.

In order to achieve the same, the disclosure provides a hemostatic device including a band for being wrapped around a hemostasis-requiring site of a limb, securing means for securing the band in a state where the band is wrapped around the limb, and an inflation portion that interlocks with the band, and that is inflated by injecting gas. The inflation portion has a first layer formed of a thermosetting elastomer and a second layer which covers an outer surface of the first layer. The first layer is formed of a material which has a larger gas permeation amount per unit area than a material for forming the second layer. The second layer has a gap portion which can expose the outer surface of the first layer outward from the second layer in a state where the inflation portion is inflated.

According to the hemostatic device configured as described above, after the inflation portion is inflated, the outer surface of the first layer can be exposed outward from the second layer via the gap portion of the second layer. In this case, the first layer is formed of the material which has the larger gas permeation amount per unit area than the material for forming the second layer. Therefore, in the inflation portion, while the compressing force acting on the hemostasis-requiring site is maintained via the first layer, the gas contained inside the inflation portion is discharged outward from the inflation portion with the lapse of time. In addition, the inflation portion has a double layer structure including the first layer and the second layer. Accordingly, it is possible to improve the strength of the inflation portion. Therefore, the hemostatic device can satisfactorily maintain the strength of the inflation portion, does not need to be operated by a physician or a nurse, and can reduce the compressing force acting on the hemostasis-requiring site with the lapse of time to such an extent that the vascular occlusion can be prevented.

DETAILED DESCRIPTION

Hereinafter, an exemplary embodiment of the disclosure will be described with reference to the accompanying drawings. Note that, the following description does not limit the technical scope or the meaning of terms described in the appended claims. In addition, dimensional proportions in the drawings are exaggerated and may be different from actual proportions for convenience of description, in some cases.

Figure 4:
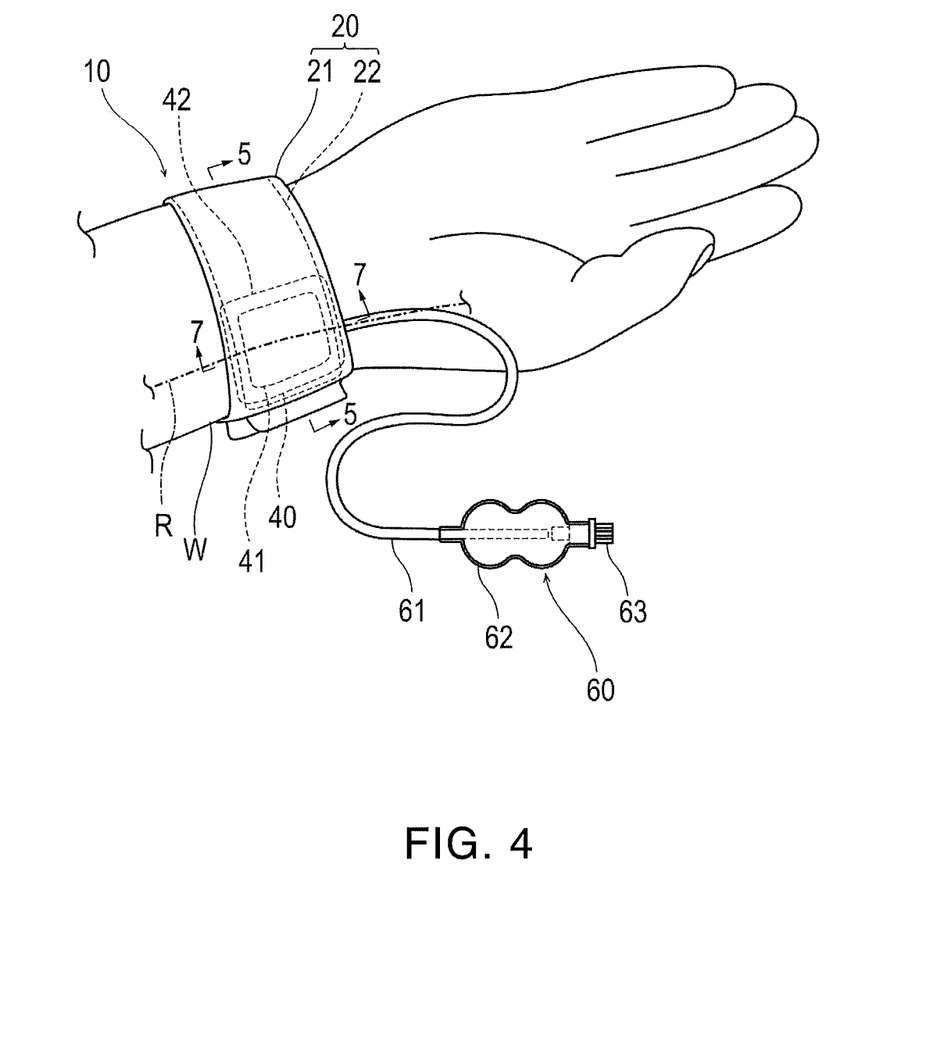
FIG. 4 is a perspective view illustrating a state where the hemostatic device according to the exemplary embodiment is worn on a wrist.
Figure 6:
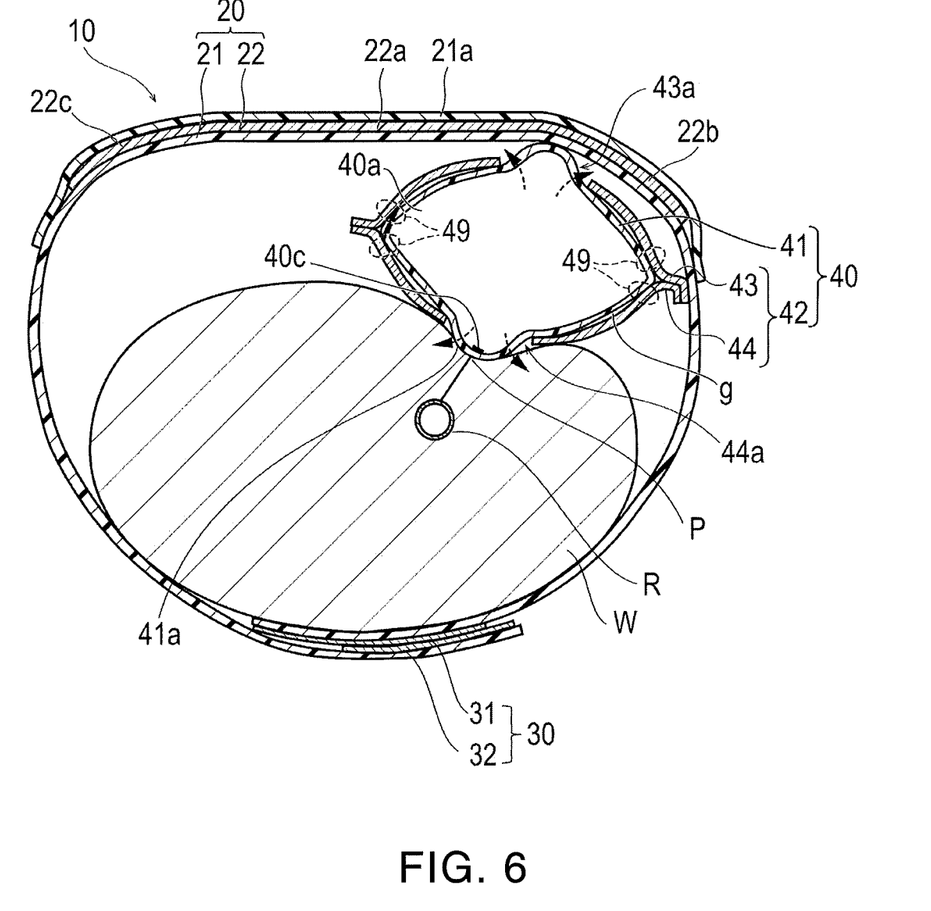
FIG. 6 is a view illustrating a state where an outer surface of a first layer is exposed outward from a second layer.

As illustrated in FIGS. 4 and 6, a hemostatic device 10 according to the exemplary embodiment of the disclosure herein is used for performing hemostasis on a puncture site P (corresponding to a "hemostasis-requiring site") formed in a radial artery R of a wrist W (corresponding to a "limb") in order to insert a catheter for performing treatment and examination into a blood vessel, after an introducer sheath indwelling the puncture site P is removed.

Figure 1:
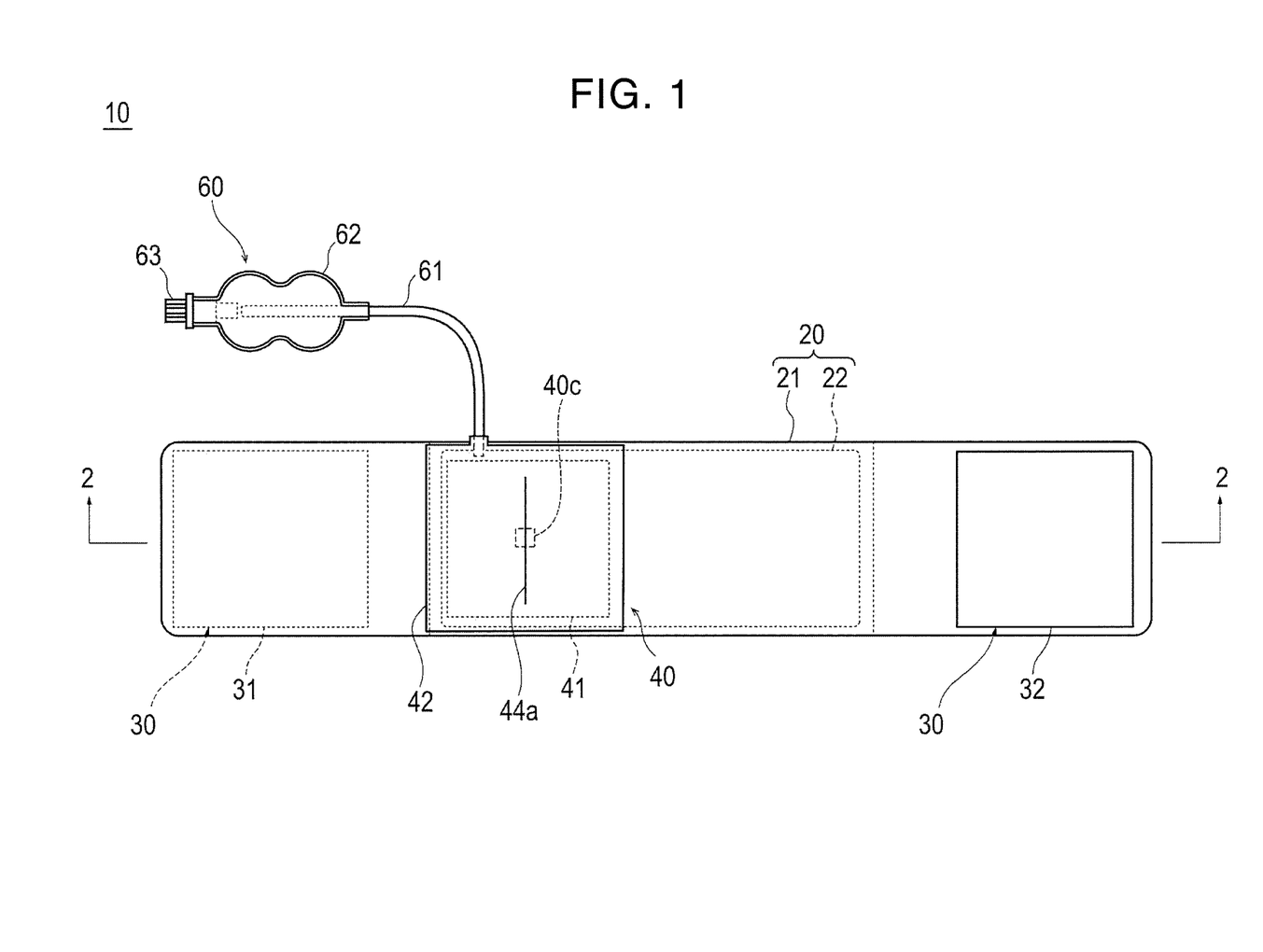
FIG. 1 is a plan view when a hemostatic device according to an exemplary embodiment of the disclosure is viewed from an inner surface side.
Figure 2:
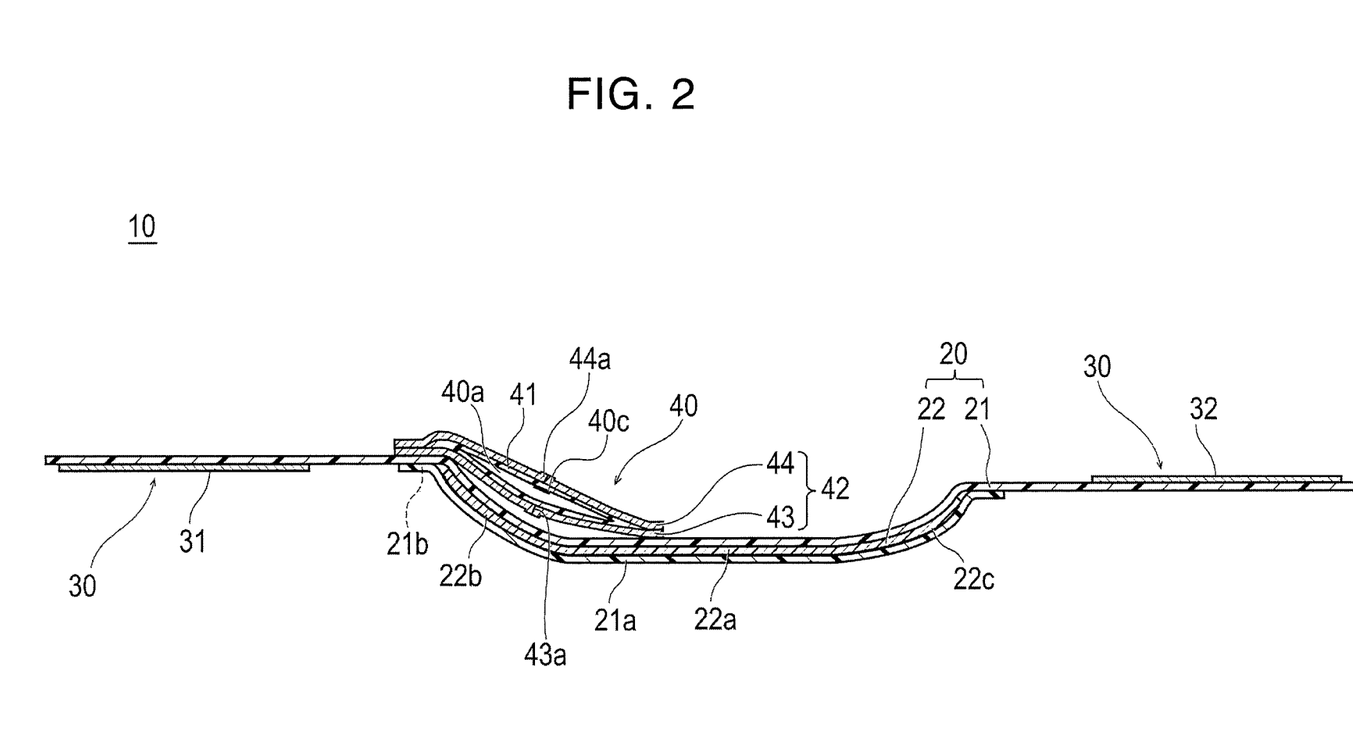
FIG. 2 is a sectional view taken along line 2-2 in FIG. 1.

As illustrated in FIGS. 1 and 2, the hemostatic device 10 has a band 20 for being wrapped around the wrist W, a surface fastener 30 (corresponding to "securing means") for securing the band 20 in a state where the band 20 is wrapped around the wrist W, an inflation portion 40 that is inflated by injecting gas so as to compress the puncture site P, a marker 40c for aligning the inflation portion 40 with the puncture site P, and an injection portion 60 that can inject gas into the inflation portion 40.

Note that, in the description herein, when the band 20 is in a state of being wrapped around the wrist W, a side (wearing surface side) facing a body surface of the wrist W in the band 20 is referred to as an "inner surface", and a side opposite thereto is referred to as an "outer surface side".

The band 20 includes a belt 21 configured to include a flexible belt-like member, and a support plate 22 which is more rigid than the belt 21.

Figure 5A:
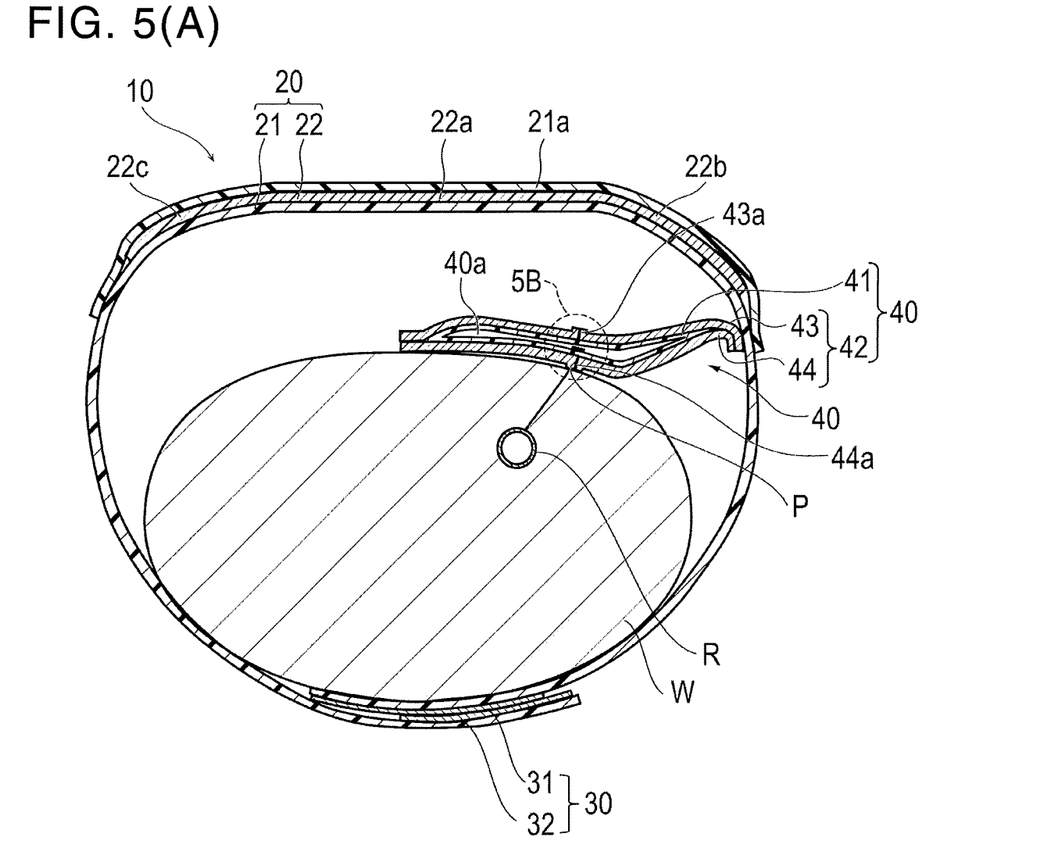
FIG. 5(A) is a sectional view taken along line 5-5 in FIG. 4.
Figure 5B:
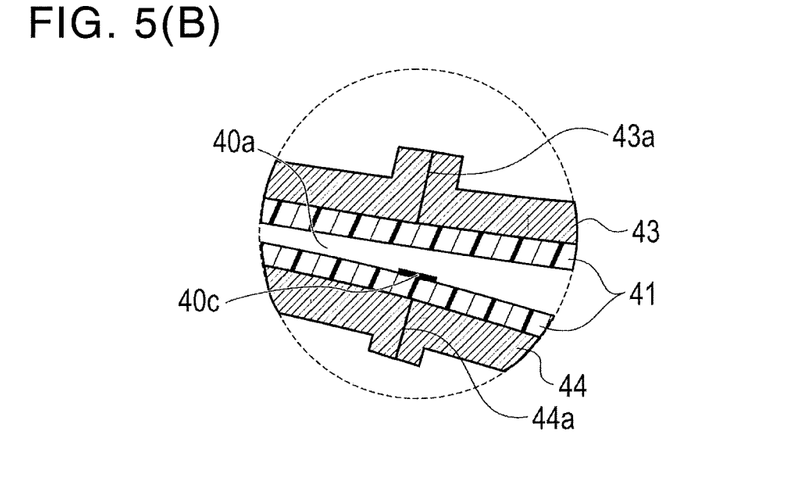
FIG. 5(B) is a partial enlarged view in the reference numeral 5B in FIG. 5(A).

As illustrated in FIGS. 4 to 6, the belt 21 is wrapped substantially one time around an outer periphery of the wrist W. As illustrated in FIG. 2, a support plate holder 21a for holding the support plate 22 is formed in a central portion of the belt 21. The support plate holder 21a is adapted to have a double layer construction in such a way that a separate belt-like member is joined to the outer surface side (or the inner surface side) by means of fusion bonding (heat-welding, high frequency fusion, or ultrasound fusion) or adhesion (adhesion using an adhesive or a solvent), thereby holding the support plate 22 inserted into a gap or pocket formed between the double layer structure.

A male side (or a female side) 31 of the surface fastener 30, such as a hook and loop fastener (e.g., a product commonly known as VELCRO® or Magic Tape in Japan, is disposed on the outer surface side of a portion in the vicinity of the left end in FIG. 1 of the belt 21, and a female side (or a male side) 32 of the surface fastener 30 is disposed on the inner surface side of a portion in the vicinity of the right end in FIG. 1 of the belt 21. As illustrated in FIGS. 5 and 6, the belt 21 is wrapped around the wrist W, and the male side 31 and the female side 32 are joined to each other. In this manner, the band 20 is worn on the wrist W. Note that, without being limited to the surface fastener 30, means for securing the band 20 in a state where the band 20 is wrapped around the wrist W may be a snap, a button, a clip, or a frame member passing through the end portion of the belt 21, for example.

A configuration material of the belt 21 is not particularly limited as long as the material is flexible. For example, these materials include polyolefin such as polyvinyl chloride, polyethylene, polypropylene, polybutadiene, and ethylene-vinyl acetate copolymer (EVA), polyester such as polyethylene terephthalate (PET) and polybutylene terephthalate (PBT), various thermoplastic elastomers such as polyvinylidene chloride, silicone, polyurethane, polyamide elastomer, polyurethane elastomer, and polyester elastomer, or any optional combination thereof (blend resin, polymer alloy, and laminate).

Note that, in a case where the inflation portion 40 (to be described later) is configured to include a thermoplastic material, the belt 21 can interlock with the inflation portion 40 by means of fusion bonding. Accordingly, it is preferable that the belt 21 is configured to include the thermoplastic material. Note that, in the belt 21, an interlock region 21b (in the exemplary embodiment, as illustrated in FIG. 2, a region between a region having a first curved portion 22b of the support plate 22 (to be described later) and a region to which the male side 31 of the surface fastener 30 is attached) with which at least the inflation portion 40 interlocks may be configured to include the thermoplastic material. A portion other than the interlock region 21b may be formed of a material other than the thermoplastic material.

In addition, it is preferable that the belt 21 is configured to include a material having higher elastic modulus than a material configuring a first layer 41 of the inflation portion 40 (to be described later). For example, in a case where the first layer 41 of the inflation portion 40 is configured to include a silicone rubber, a thermoplastic material can be used as the configuration material of the belt 21. For example, as the thermoplastic material, it is possible to use a thermoplastic resin such as polyvinyl chloride, polyethylene, polypropylene, and polyvinylidene chloride, or various thermoplastic elastomers such as olefinic thermoplastic elastomer and styrene thermoplastic elastomer. Since the belt 21 is formed of this material, the belt 21 is relatively less likely to stretch. Without being affected by a wearer's size of the wrist W, it is possible to suitably maintain a state where the inflation portion 40 is wrapped around the wrist W.

In addition, it is preferable that a portion overlapping at least the inflation portion 40 in the belt 21 is substantially transparent. However, without being limited to transparency, the portion may be translucent or colored transparent. In this manner, the puncture site P is visible from the outer surface side, thereby enabling the marker 40c (to be described later) to easily align with the puncture site P.

As illustrated in FIG. 2, the support plate 22 is inserted between the support plate holder 21a formed to have the double structures of the belt 21. In this manner, the support plate 22 is held by the belt 21. The support plate 22 has a plate shape in which at least a portion thereof is curved toward the inner surface side (wearing surface side). The support plate 22 is configured to include a material which is more rigid than that of the belt 21, and is adapted to maintain a substantially constant shape. The method of providing the support plate 22 in or on the belt 21 is not limited to the illustrated arrangement, and may involve joining the support plate 22 to the inner surface side or the outer surface side of the band 20 by a suitable method such as welding or adhesion. Also, another acceptable arrangement is one in which the belt 21 is connected to both ends of the support plate 22. It is thus not necessary for a portion of the belt 21 to overlap with the support plate 22.

The support plate 22 has a long shape in the longitudinal direction of the belt 21. A central portion 22a in the longitudinal direction of the support plate 22 is hardly curved, and has a flat plate or generally planar shape. Both sides of the central portion 22a respectively have a first curved portion 22b (left side in FIG. 2) and a second curved portion 22c (right side in FIG. 2) which are curved toward the inner surface side and along the longitudinal direction (circumferential direction of the wrist W) of the belt 21.

By way of example, configuration materials of the support plate 22 include acrylic resin, polyvinyl chloride (particularly, rigid polyvinyl chloride), polyethylene, polypropylene, polyolefin such as polybutadiene, polystyrene, poly-(4-methylpentene-1), polycarbonate, ABS resin, polymethyl methacrylate (PMMA), polyacetal, polyacrylate, polyacrylonitrile, polyvinylidene fluoride, ionomer, acrylonitrile-butadiene-styrene copolymer, polyethylene terephthalate (PET), polyester such as polybutylene terephthalate (PBT), butadiene-styrene copolymer, aromatic or aliphatic polyamide, and fluorine-based resin such as polytetrafluoroethylene.

Similar to the belt 21, in the support plate 22, it is preferable that a portion overlapping the inflation portion 40 is substantially transparent. However, without being limited to transparency, the portion may be translucent or colored transparent. In this manner, the puncture site P is reliably visible from the outer surface side, thereby enabling the marker 40c (to be described later) to easily align with the puncture site P. Note that, the support plate 22 may not have a portion which has a flat plate shape like the central portion 22a, that is, the support plate 22 may be curved over the entire length.

The inflation portion 40 is provided with a function to apply a compressing force to the puncture site P after being inflated by injecting gas, and a function to reduce the compressing force acting on the puncture site P with the lapse of time by discharging the injected gas outward with the lapse of time. Note that, as long as the inflation portion 40 can be inflated, the gas injected into the inflation portion 40 is not particularly limited. For example, air can be used.

As illustrated in FIG. 2, the inflation portion 40 has the first layer 41 and a second layer 42 which covers an outer surface of the first layer 41.

Figure 3:
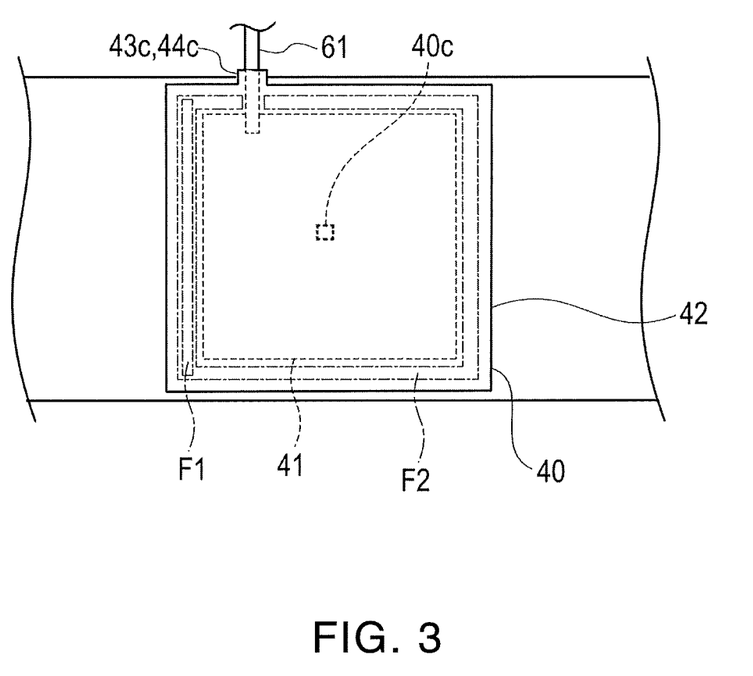
FIG. 3 is a plan view illustrating an inflation portion of the hemostatic device according to the exemplary embodiment of the disclosure.

The first layer 41 is formed of a material which has a larger gas permeation amount per unit area than a material for forming the second layer 42. Specifically, it is preferable that the first layer 41 is formed of a thermosetting elastomer. As illustrated in FIGS. 1 and 3, the first layer 41 is provided with a substantially rectangular outer shape in a plan view. As illustrated in FIG. 6, the first layer 41 is configured so that the first layer 41 can be exposed outward from the second layer 42 via gap portions 43a and 44a of the second layer 42 (to be described later), when the inflation portion 40 is inflated. More specifically, the first layer 41 is configured to protrude from the gap portions 43a and 44a, when the inflation portion 40 is inflated.

The outer surface of the first layer 41 is secured to an inner surface of the second layer 42 at a location within the second layer 42, except for the gap portion 44a included in a second sheet 44 of the second layer 42 (to be described later). Therefore, when the first layer 41 protrudes from the gap portions 43a and 44a, it is possible to prevent the whole first layer 41 from being exposed from the inside of the second layer 42.

Note that, it is preferable that the first layer 41 and the second layer 42 are secured to each other at one or more locations in order to prevent the whole first layer 41 from being exposed from the inside of the second layer 42, when the inflation portion 40 is inflated. In addition, in order that the first layer 41 is exposed from the gap portions 43a and 44a when the inflation portion 40 is inflated, it is preferable that the outer surface of the first layer 41 is secured to the inner surface of the second layer 42 at a location other than the gap portions 43a and 44a in the second layer 42. According to the exemplary embodiment, as illustrated in FIG. 6, securing portions 49 are respectively disposed at four locations of an end portion (end portion of the inflation portion 40 along a width direction of the band 20) of the inflation portion 40 located in a lateral direction in the drawing so as to form a predetermined gap g between the first layer 41 and the second layer 42, in a state where the inflation portion 40 is inflated. That is, the first layer 41 and the second layer 42 are not secured to one another except at the securing portions 49. Thus, in a state where the inflation portion 40 is not inflated, the inflation portion 40 has a gap between the first layer 41 and the second layer 42. Additionally, when the inflation portion 40 is inflated and then the gap portions 43a, 44a are opened, the second layer 42, having been enlarged by the first layer 41, then returns to its original shape due to contraction of the second layer 41. Thus, the inflation portion 40 forms a gap g between the first layer 41 and the second layer 42.]

The gap g formed between the first layer 41 and the second layer 42 causes the gas contained inside the first layer 41 to be discharged (permeated) outward via the gap g. Therefore, a discharge rate of the gas discharged from the first layer 41 can be properly adjusted by properly adjusting a surface area exposed from the second layer 42 by the first layer 41, thickness of the first layer 41, or a size of the gap g.

In addition, the second layer 42 may include at least one or more gap portions. In this case, for the following reason, it is preferable to dispose the gap portion on the first sheet 43 side of the second layer 42. If the gap portion 43a is formed on a surface (surface on a side facing the band 20) on the first sheet 43 side of the second layer 42, when the first layer 41 protrudes from the gap portion 43a, a space can be formed between the inflation portion 40 and the band 20. In this manner, the gas can be efficiently discharged from the first layer 41.

As illustrated in FIG. 2, the second layer 42 is configured to cover the first layer 41, in a state before the inflation portion 40 is inflated. In addition, as illustrated in FIG. 6, the second layer 42 is configured so that a portion of the first layer 41 protrudes from the second layer 42, in a state where the inflation portion 40 is inflated.

The second layer 42 is configured to include a material having a smaller gas permeation amount per unit area than a material configuring the first layer 41. Specifically, in a case where the material configuring the first layer 41 is a thermosetting elastomer, it is preferable that the second layer 42 is formed of a thermoplastic resin which has lower gas permeability than the thermosetting elastomer configuring the first layer 41. For example, as the thermoplastic resin, it is possible to use polyvinyl chloride, polyethylene, polypropylene, and polyvinylidene chloride.

As illustrated in FIGS. 2 and 3, the second layer 42 is configured in a bag-like shape in which the first sheet 43 and the second sheet 44 overlap each other.

As illustrated in FIGS. 1 and 3, the first sheet 43 and the second sheet 44 are provided with a substantially rectangular outer shape which is slightly larger than the first layer 41 in a plan view.

As illustrated in FIG. 6, the first sheet 43 has the gap portion 43a which can expose the outer surface of the first layer 41 outward from the first sheet 43, in a state where the inflation portion 40 is inflated. According to the exemplary embodiment, the size of the gap portion 43a is appropriately adjusted. In this manner, it is possible to adjust the amount of the first layer 41 protruding from the gap portion 43a. Note that, the outer surface of the first layer 41 protruding from the gap portion 43a may come into contact with the belt 21.

As illustrated in FIGS. 2 and 5, the gap portion 43a is configured to be closed by being temporarily secured in a state before the inflation portion 40 is inflated. Although the securing method is not particularly limited, an adhering method using an adhesive may be used, for example. The gap portion 43a is switched from a closed state to an open state when the inflation space 40a inside the inflation portion 40 reaches a predetermined pressure. That is, the gap portion 43a in the closed state is opened when the inflation space 40a inside the inflation portion 40 reaches the predetermined pressure. Therefore, the inflation portion 40 can prevent initial decompression, and can appropriately adjust a starting time of automatic decompression.

As illustrated in FIG. 6, the second sheet 44 has the gap portion 44a which can expose the outer surface of the first layer 41 outward from the second sheet 44, in a state where the inflation portion 40 is inflated. The outer surface of the first layer 41 protruding from the gap portion 44a comes into contact with the puncture site P. According to the exemplary embodiment, the size of the gap portion 44a is appropriately adjusted. In this manner, it is possible to adjust the amount of the first layer 41 protruding from the gap portion 44a.

As illustrated in FIGS. 2 and 5, the gap portion 44a is configured to be closed by being temporarily secured in a state before the inflation portion 40 is inflated. Although the securing method is not particularly limited, an adhering method using an adhesive may be used, for example. The gap portion 44a is switched from a closed state to an open state when the inflation space 40a inside the inflation portion 40 reaches a predetermined pressure. That is, the gap portion 44a in the closed state is opened when the inflation space 40a inside the inflation portion 40 reaches the predetermined pressure. Therefore, the inflation portion 40 can prevent initial decompression, and can appropriately adjust a starting time of automatic decompression.

Figure 7:
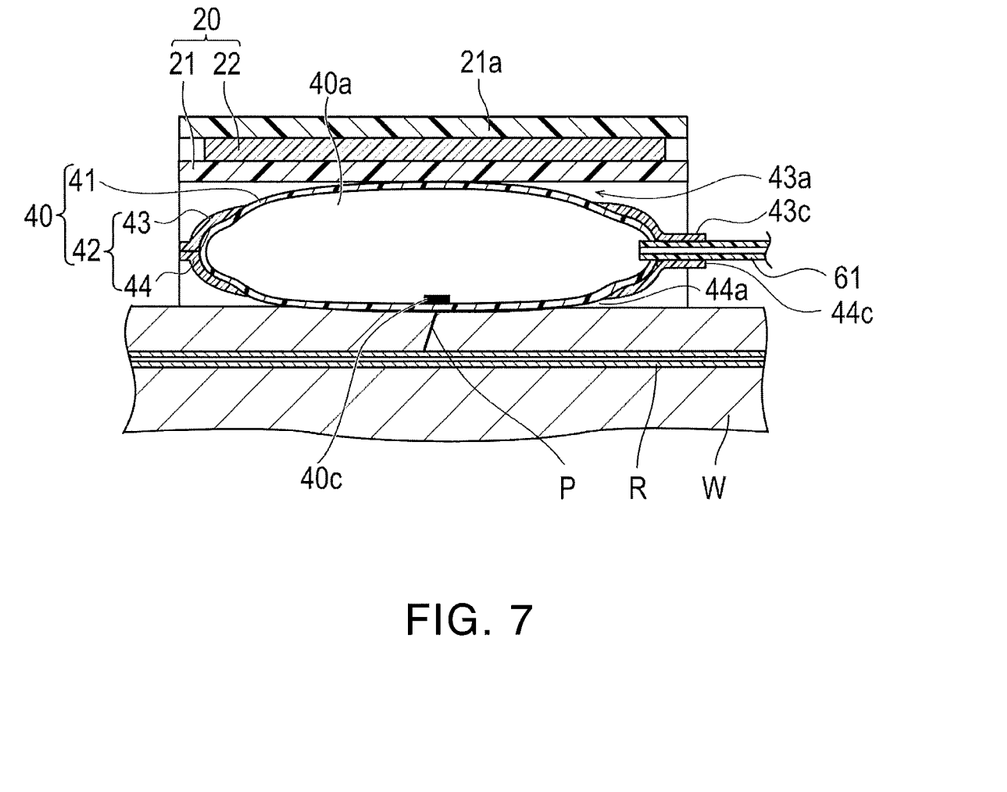
FIG. 7 is a sectional view taken along line 7-7 in FIG. 4.

As illustrated in FIG. 3, the first sheet 43 has a protruding portion 43c protruding outward from a rectangular portion in a plan view. Similarly, as illustrated in FIG. 3, the second sheet 44 has a protruding portion 44c protruding outward from a rectangular portion in a plan view. As illustrated in FIGS. 3 and 7, the tube 61 of the injection portion 60 (to be described later) is disposed between the protruding portion 43c of the first sheet 43 and the protruding portion 44c of the second sheet 44. The protruding portions 43c and 44c adhere to the tube 61 by using an adhesive. In this manner, the tube 61 is held by the inflation portion 40. Note that, an outer shape of the first sheet 43 and the second sheet 44 is not particularly limited to the above-described shape. For example, circular, elliptical, and polygonal shapes may be employed. In addition, the protruding portions 43c and 44c may not be provided.

At least a portion of the first sheet 43 and the second sheet 44 is fused to the interlock region 21b of the belt 21. According to the exemplary embodiment, as illustrated in FIG. 2, the inflation portion 40 is disposed in a state where the first sheet 43 faces the inner surface side of the band 20. Accordingly, one side of the first sheet 43 is fused to the inner surface side of the interlock region 21b of the band 20. Hereinafter, a fusion portion between the inflation portion 40 and the band 20 is referred to as a "first fusion portion F1" (refer to FIG. 3). In a case where the second layer 42 of the inflation portion 40 is formed of a thermoplastic resin, the first sheet 43 formed of the thermoplastic resin is fused to the interlock region 21b of the band 20 formed of the thermoplastic resin. In this manner, the inflation portion 40 and the band 20 can interlock with each other by means of fusion bonding.

Furthermore, according to the exemplary embodiment, as illustrated in FIG. 3, the peripheral edge portion of the first sheet 43 and the peripheral edge portion of the second sheet 44 can be fused to each other except for a portion into which the tube 61 of the injection portion 60 (to be described later) is inserted. Hereinafter, a fusion portion between the peripheral edge portion of the first sheet 43 and the peripheral edge portion of the second sheet 44 is referred to as a "second fusion portion F2". Note that, the peripheral edge portion of the first sheet 43 and the peripheral edge portion of the second sheet 44 may adhere to each other by using an adhesive.

Since the thermoplastic material used for the first sheet 43 is the same material as the thermoplastic material used for the interlock region 21b of the band 20, a binding force between the first sheet 43 and the band 20 in the first fusion portion F1 can be strengthened. However, the thermoplastic material used for the first sheet 43 and the thermoplastic material used for the interlock region 21b of the band 20 may be different from each other. In addition, since the thermoplastic material used for the first sheet 43 is the same material as the thermoplastic material used for the second sheet 44, a binding force between the first sheet 43 and the second sheet 44 in the second fusion portion F2 can be strengthened. However, the thermoplastic material used for the first sheet 43 and the thermoplastic material used for the second sheet 44 may be different from each other.

The thermosetting elastomer used for the first layer 41 is provided with higher gas permeability than the thermoplastic resin used for the second layer 42. Therefore, as illustrated in FIG. 6, in a state where the first layer 41 protrudes via the gap portions 43a and 44a after the inflation portion 40 is inflated, the gas contained inside the inflation portion 40 is discharged outward from the inflation portion 40 with the lapse of time via the first layer 41 to such an extent that the vascular occlusion can be prevented. Therefore, even if a physician or a nurse does not perform the decompressing operation, the compressing force applied to the puncture site P by the inflation portion 40 can be decreased with the lapse of time. As a result, it is possible to reduce the treatment burden or labor cost of the physician or the nurse. In addition, the first layer 41 formed of the thermosetting elastomer has the relatively high gas permeability. Accordingly, it is not necessary to excessively reduce the thickness of the inflation portion 40 in order to increase the gas permeation amount, and it is possible to satisfactorily maintain the strength of the inflation portion 40.

It is preferable that a gas permeability coefficient of the thermosetting elastomer used for the first layer 41 is ten times or more greater than a gas permeability coefficient of the thermoplastic material used for the second layer 42, more preferably 100 times or more, and most preferably 1,000 times or more. In this manner, since a difference in the gas permeability coefficient between the first layer 41 and the second layer 42 is used, the hemostatic device 10 can suitably adjust the compressing force which is applied to the puncture site P by the inflation portion 40 and which is reduced with the lapse of time. In addition, from a viewpoint of the gas permeability coefficient, it is preferable that the thermoplastic material used for the second layer 42 is the thermoplastic resin. Note that, in the exemplary embodiment, the gas permeability coefficient means a permeability coefficient of mixed gas of oxygen and nitrogen (volume ratio of oxygen to nitrogen=20:80).

In addition, the thermoplastic resin used for the second layer 42 has a higher elastic modulus than the thermosetting elastomer used for the first layer 41. Therefore, the first layer 41 can be stretched and easily protruded from the gap portion 44a, thereby enabling the first layer 41 to locally apply the compressing force to the wrist W.

In addition, in order to obtain a sufficient hemostasis effect, it is preferable to maintain a state where the puncture site P is compressed by the inflation portion 40 for four hours after the inflation portion 40 is inflated. In addition, in order to prevent vascular occlusion while the puncture site P is compressed, the internal pressure of the inflation portion 40 is decompressed with the lapse of time. In this manner, it is preferable to reduce the compressing force applied to the puncture site P by the inflation portion 40 with the lapse of time. In order that the compressing force acting on the puncture site P is changed with the lapse of time to the same extent when the decompressing operation is performed using a dedicated instrument such as a syringe in the known art, it is preferable to set a type, a thickness, and a surface area of the thermosetting elastomer of the first layer 41 protruding from the gap portions 43a and 44a so as to satisfy the following two conditions:

(Condition 1) In a state where the band 20 is wrapped around the wrist W, the gas has to be discharged outward from the inflation portion 40 via the first layer 41 over four hours after the inflation portion 40 is inflated. After every one hour elapses, internal pressure of the inflation portion 40 reaches 70% to 97% (preferably, 75% to 94%) of the internal pressure of the inflation portion 40 one hour ago;

(Condition 2) In a state where the band 20 is wrapped around the wrist W, the internal pressure inside the inflation portion 40 after four hours elapses from the inflation reaches 30% to 80% (preferably, 40% to 71%) of the initial internal pressure of the inflation portion.

Note that, Condition 1 and Condition 2 may be substituted with Condition 3 and Condition 4 below:

(Condition 3) In a state where the band 20 is wrapped around the wrist W, the gas has to be discharged outward from the inflation portion 40 via the first layer 41 over four hours after the inflation portion 40 is inflated. After every one hour elapses, the gas volume injected into the inflation portion 40 reaches 85% to 96% (preferably, 88% to 96%) of gas volume inside the inflation portion 40 one hour ago;

(Condition 4) In a state where the band 20 is wrapped around the wrist W, the gas volume inside the inflation portion 40 after four hours elapses from the inflation reaches 55% to 95% (preferably, 60% to 80%) of the initial gas volume inside the inflation portion 40.

In order to satisfy Condition 1 and Condition 2 (or Condition 3 and Condition 4) described above, it is necessary to appropriately set the thickness and the surface area of the first layer 41. For example, in a case where the film thickness of the inflation portion is approximately 0.5 mm and the entire surface area is 16 $cm^2$, it is possible to form the first layer 41 by using a thermosetting elastomer whose gas permeability coefficient is 75 to $550\times10^{-8}$ cc·cm/$cm^2$·sec·atm (preferably, 200 to $400\times10^{-8}$ cc·cm/$cm^2$·sec·atm). For example, this material includes silicone rubber.

In this way, the inflation portion 40 has the first layer 41 formed of the thermosetting elastomer, and the second layer 42 which covers the outer surface of the first layer 41 and which is formed of the thermoplastic resin having the lower gas permeability than the thermosetting elastomer. The second layer 42 has the gap portions 43a and 44a which can expose the outer surface of the first layer 41 outward from the second layer 42 in a state where the inflation portion 40 is inflated. Therefore, after the inflation portion 40 is inflated, the gas contained inside the inflation portion 40 is discharged outward from the inflation portion 40 with the lapse of time via the first layer 41 formed of the thermosetting elastomer to such an extent that the vascular occlusion can be prevented.

Note that, as described above, the inflation portion 40 is disposed on the inner surface side of the band 20. Therefore, if the inflation portion 40 is inflated, the band 20 restrains the inflation portion 40 from being inflated in a direction separated from the body surface of the wrist W. In this manner, the compressing force of the inflation portion 40 is concentrated on the wrist W side. Accordingly, it is possible to suitably apply the compressing force to the puncture site P. In addition, the inflation portion 40 is wrapped around the wrist W by the band 20, and the internal pressure increases. Accordingly, the gas contained inside the inflation portion 40 can be suitably discharged outward. Furthermore, it is possible to suitably prevent the discharge of the gas contained inside the inflation portion 40 from being hindered in such a way that a patient wearing the hemostatic device 10 inadvertently touches the first layer 41.

Further, it is preferable that the inflation portion 40 is substantially transparent. However, without being limited to transparency, the portion may be translucent or colored transparent. In this manner, the puncture site P is visible from the outer surface side, thereby enabling the marker 40c (to be described later) to easily align with the puncture site P.

As illustrated in FIG. 2, the marker 40c is disposed on the inner surface of the first layer 41. Since this marker 40c is disposed in the inflation portion 40, the inflation portion 40 can easily align with the puncture site P. Accordingly, misalignment of the inflation portion 40 is restrained. In addition, since the marker 40c is disposed on the inner surface side of the first layer 41, the marker 40c does not directly come into contact with the puncture site P. Note that, a position for disposing the marker 40c is not particularly limited as long as the inflation portion 40 can align with the puncture site P.

Without being particularly limited, a shape of the marker 40c includes circular, triangular, and square shapes, for example. In the exemplary embodiment, the marker 40c has the square shape.

A size of the marker 40c is not particularly limited. However, for example, in a case where the shape of the marker 40c is the square shape, it is preferable that one side length thereof is in a range of 1 to 4 mm. If one side length is 5 mm or longer, the size of the marker 40c is larger than the size of the puncture site P. Consequently, the central portion of the inflation portion 40 is less likely to align with the puncture site P.

Without being particularly limited, a material of the marker 40c includes oily colorants such as ink, and resins kneaded with pigments.

A color of the marker 40c is not particularly limited as long as the color enables the inflation portion 40 to align with the puncture site P. However, it is preferable that the color is a green color system. If the green color system is used, the marker 40c is easily visible on the blood or the skin. Accordingly, the inflation portion 40 is much likely to align with the puncture site P.

In addition, it is preferable that the marker 40c is translucent or colored transparent. In this manner, the puncture site P is visible from the outer surface side of the marker 40c.

A method of disposing the marker 40c in the inflation portion 40 is not particularly limited. However, for example, the method includes a method of printing the marker 40c on the inflation portion 40, and a method of attaching the marker 40c to the inflation portion 40 by applying an adhesive to one side surface of the marker 40c.

The injection portion 60 is used for injecting the gas into the inflation portion 40. As illustrated in FIG. 1, the injection portion 60 is connected to the inflation portion 40.

The proximal portion of the injection portion 60 is connected to the inflation portion 40. The injection portion 60 includes a flexible tube 61 whose lumen communicates with the inside of the inflation portion 40, a bag 62 which is disposed in the distal portion of the tube 61 so as to communicate with the lumen of the tube 61, and a tubular connector 63 connected to the bag 62 and which has a check valve (not illustrated) incorporated therein.

As illustrated in FIGS. 3 and 7, the tube 61 is connected to the inflation portion 40 so as to be interposed between the protruding portion 43c of the first sheet 43 and the protruding portion 44c of the second sheet 44. However, a connecting position of the tube 61 to the inflation portion 40 is not particularly limited as long as the lumen of the tube 61 communicates with the internal space of the inflation portion 40.

When the inflation portion 40 is inflated, a distal tubular portion of a syringe (not illustrated) is inserted into the connector 63 so as to open the check valve. A plunger of the syringe is pressed, and the gas contained in the syringe is injected into the inflation portion 40 via the injection portion 60. If the inflation portion 40 is inflated, the bag 62 communicating with the inflation portion 40 via the tube 61 is inflated. It is possible to visually confirm that the inflation portion 40 can be pressurized without leakage of the gas. If the distal tubular portion of the syringe is removed from the connector 63 after the gas is injected into the inflation portion 40, the check valve incorporated in the connector 63 is closed, thereby preventing the leakage of the gas.

Next, a method of using the hemostatic device 10 according to the exemplary embodiment will be described.

Before the hemostatic device 10 is worn on the wrist W, the inflation portion 40 is in a non-inflated state as illustrated in FIG. 2. As illustrated in FIGS. 4 and 5, in a case where the radial artery R of the wrist W of the right hand is punctured, the puncture site P is located at a position close to the thumb side. Normally, the introducer sheath indwells the puncture site P. The band 20 is wrapped around the wrist W left in a state where the introducer sheath indwells the puncture site P. The marker 40c disposed in the inflation portion 40 aligns with the inflation portion 40 and the band 20 so as to overlap the puncture site P from above. The male side 31 and the female side 32 of the surface fastener 30 are brought into contact with and joined to each other. In this manner, the band 20 is worn on the wrist W.

In this case, the hemostatic device 10 is worn on the wrist W so that the injection portion 60 faces the downstream side (palm side) of the blood flow in the radial artery R. In this manner, the injection portion 60 can be operated without interfering with a manual skill on the upstream side from the wrist or an instrument (for example, a blood pressure monitor) located on the upstream side. In addition, the hemostatic device 10 is worn on the wrist W of the right hand so that the injection portion 60 faces downstream side. In this manner, the inflation portion 40 is located in the radial artery R located close to the thumb side of the wrist W. Note that, in a case of the artery, the upstream side of the blood vessel indicates a direction closer to the heart of the blood vessel. In addition, the downstream side of the blood vessel indicates a direction farther away from the heart of the blood vessel.

Note that, the hemostatic device 10 may be used in a case where the radial artery of the wrist of the left hand is punctured. In this case, the injection portion 60 is worn on the wrist W of the left hand so as to face the upstream side of the blood flow in the radial artery.

After hemostatic device 10 is worn on the wrist W, the syringe (not illustrated) is connected to the connector 63 of the injection portion 60. As described above, the gas is injected into the inflation portion 40, and the inflation portion 40 is inflated.

In this case, as illustrated in FIG. 6, when the inflation space 40a inside the inflation portion 40 reaches a predetermined pressure, the inflation portion 40 opens the gap portions 43a and 44a. Then, the outer surface of the first layer 41 protrudes from the gap portion 43a and comes into contact with the belt 21. In addition, the outer surface of the first layer 41 protrudes from the gap portion 44a and comes into contact with and presses the puncture site P, thereby performing the hemostasis on the puncture site P.

Here, an amount of the gas injected is adjusted in accordance with a clinical case. In this manner, an inflated degree of the inflation portion 40, that is, the compressing force acting on the puncture site P can be easily adjusted. For example, in a case where the inflation portion 40 is excessively inflated since too much gas is injected into the inflation portion 40, the excessively injected gas may be discharged from the inside of the inflation portion 40 by using the syringe. As described above, since the first layer 41 of the inflation portion 40 is formed of the thermosetting elastomer, the first layer 41 is elastic. Therefore, if the gas excessively injected into the inflation portion 40 is discharged outward, the inflation portion 40 is contracted and deformed in response to the discharge. The inflation portion 40 has a desired inflation degree, and can apply the suitable compressing force to the puncture site P.

After the inflation portion 40 is inflated, the syringe is detached from the connector 63. Then, the introducer sheath is removed from the puncture site P.

As illustrated by an arrow in FIG. 6, after the inflation portion 40 is inflated, while the compressing force is applied directly to the puncture site P via the first layer 41 protruding from the gap portion 44a, the gas contained inside the inflation portion 40 is discharged outward from the inflation portion 40 with the lapse of time. Here, as described above, according to the exemplary embodiment, the size of the gap portions 43a and 44a is appropriately adjusted. In this manner, it is possible to adjust the amount of the first layer 41 protruding from the gap portions 43a and 44a. Therefore, when the gas contained inside the inflation portion 40 is discharged outward from the inflation portion 40 via the first layer 41, the gas permeation amount can be appropriately adjusted.

Note that, in a case where the hemostasis is not sufficiently performed after the inflation portion 40 is inflated, the internal pressure of the inflation portion 40 may be increased by injecting additional gas into the inflation portion 40. For example, in a case where the internal pressure of the inflation portion 40 needs to restore the internal pressure to when the gas is injected into the inflation portion 40, additional gas may be injected to correspond to the amount of gas discharged from the inflation portion 40.

If the hemostasis is completely performed on the puncture site P after a predetermined time elapses, the hemostatic device 10 is detached from the wrist W. The hemostatic device 10 is detached from the wrist W by separating the male side 31 and the female side 32 of the surface fastener 30 from each other.

As described above, the hemostatic device 10 according to the exemplary embodiment has the band 20 for being wrapped around the puncture site P of the wrist W, the securing means 30 for securing the band 20 in a state where the band 20 is wrapped around the wrist W, and the inflation portion 40 that interlocks with the band 20, and that is inflated by injecting the gas. The inflation portion 40 has the first layer 41 and the second layer 42 which covers the outer surface of the first layer 41. The first layer 41 is formed of the material which has a larger gas permeation amount per unit area than the material for forming the second layer 42. The second layer 42 has the gap portions 43a and 44a which can expose the outer surface of the first layer 41 outward from the second layer 42 in a state where the inflation portion 40 is inflated.

According to the hemostatic device 10 configured as described above, after the inflation portion 40 is inflated, the outer surface of the first layer 41 can be exposed outward from the second layer 42 via the gap portions 43a and 44a of the second layer 42. In this case, the first layer 41 is formed of the material which has the larger gas permeation amount per unit area than the material for forming the second layer 42. Therefore, in the inflation portion 40, while the compressing force applied to the puncture site P is maintained via the first layer 41, the gas contained inside the inflation portion 40 is discharged outward from the inflation portion 40 with the lapse of time. In addition, the inflation portion 40 has the double layer structure including the first layer 41 and the second layer 42. Accordingly, it is possible to improve the strength of the inflation portion 40. Therefore, the hemostatic device 10 can satisfactorily maintain the strength of the inflation portion 40, does not need to be operated by a physician or a nurse, and can reduce the compressing force acting on the hemostasis-requiring site with the lapse of time to such an extent that the vascular occlusion can be prevented.

In addition, according to the hemostatic device 10 configured as described above, when the hemostatic device 10 is not used, the outer surface of the first layer 41 is not exposed outward from the first layer 41. Therefore, it is possible to prevent the gas permeability of the first layer 41 from becoming poor due to dust adhering to the first layer 41.

In addition, the first layer 41 is formed of the thermosetting elastomer, and the second layer 42 is formed of the thermoplastic resin having the lower gas permeability than the thermosetting elastomer. Therefore, since the first layer 41 formed of the thermosetting elastomer has the relatively high gas permeability, it is not necessary to excessively reduce the thickness of the first layer 41 in order to improve the gas permeability. Therefore, it is possible to more satisfactorily maintain the strength of the inflation portion.

In addition, the band 20 is formed of the thermoplastic resin, and has the interlock region 21b with which the inflation portion 40 interlocks. The second layer 42 of the inflation portion 40 is fused to the interlock region 21b of the band 20. Therefore, since the second layer 42 and the interlock region 21b are fused to each other, it is possible to provide the hemostatic device 10 in which the inflation portion 40 and the band 20 interlock with each other by means of fusion bonding.

In addition, at least a portion of the first layer 41 is secured to the inner surface of the second layer 42. Therefore, when the first layer 41 protrudes from the gap portions 43a and 44a, the inflation portion 40 can prevent the whole first layer 41 from being exposed from the inside of the second layer 42. In addition, since the exposure amount of the first layer 41 is adjusted, the gas discharge amount discharged from the inflation portion 40 can be more accurately controlled. Furthermore, the first layer 41 protruding from the gap portion 44a can locally compress the wrist W. Accordingly, it is possible to improve the hemostasis effect.

In addition, the first layer 41 protrudes from the gap portions 43a and 44a in a state where the inflation portion 40 is inflated. Therefore, after the inflation portion 40 is inflated, through the first layer 41 protruding from the gap portions 43a and 44a, the gas contained inside the inflation portion 40 can be more efficiently discharged outward from the inflation portion 40 with the lapse of time.

In addition, the gap portions 43a and 44a of the second layer 42 are temporarily secured so as to be openable when the inflation space 40a inside the inflation portion 40 reaches a predetermined pressure. Therefore, it is possible to prevent initial decompression, and it is possible to appropriately adjust a starting time of automatic decompression.

In addition, the gap portion 43a is formed on a surface on a side facing the band 20 in the second layer 42. Therefore, if the inflation portion 40 is inflated, the band 20 restrains the inflation portion 40 from being inflated in a direction separated from the body surface of the wrist W. In this manner, the compressing force of the inflation portion 40 is concentrated on the wrist W side. Accordingly, it is possible to suitably apply the compressing force to the puncture site P. In addition, the gap portion 43a is formed on a surface (surface on the first sheet 43 side) on the side facing the band 20 in the second layer 42. Accordingly, when the first layer 41 protrudes from the gap portion 43a, it is possible to form a space between the inflation portion 40 and the band 20. In this manner, the gas can be efficiently discharged from the first layer 41.

Figure 8:
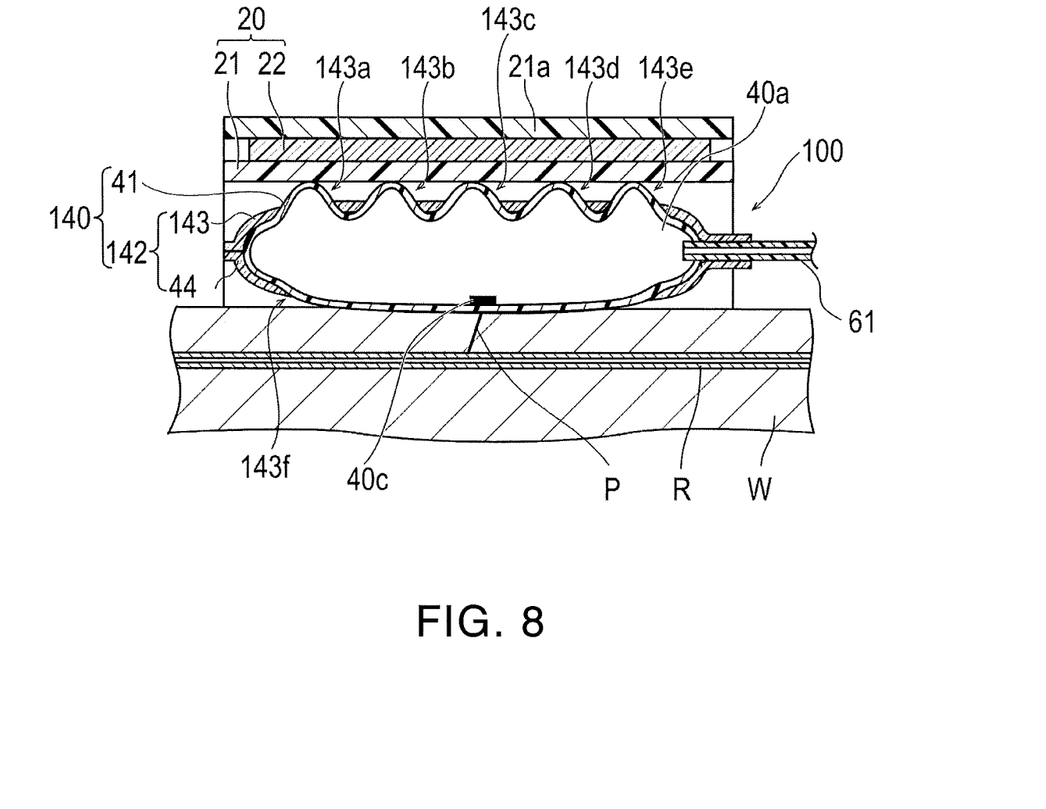
FIG. 8 is a sectional view of a hemostatic device according to a first modified exemplary embodiment.

FIG. 8 is a view corresponding to FIG. 7 of a hemostatic device 100 according to a first modified exemplary embodiment. Hereinafter, the same reference numerals will be given to configurations the same as those according to the above-described exemplary embodiment, and description thereof will be omitted.

As illustrated in FIG. 8, an inflation portion 140 included in the hemostatic device 100 according to the first modified exemplary embodiment has the first layer 41 and a second layer 142 which covers the outer surface of the first layer 41.

As illustrated in FIG. 8, the first layer 41 is configured to be exposable outward from the second layer 142 via gap portions 143a, 143b, 143c, 143d, 143e, and 143f of the second layer 142 (to be described later), when the inflation portion 140 is inflated.

The second layer 142 is configured in a bag-like shape in which a first sheet 143 and the second sheet 44 overlap each other. A configuration of the second sheet 44 is provided with the same configuration as the second sheet 44 according to the above-described exemplary embodiment, and thus, description thereof will be omitted.

As illustrated in FIG. 8, the first sheet 143 has six gap portions 143a, 143b, 143c, 143d, 143e, and 143f which can expose the outer surface of the first layer 41 outward from the first sheet 143, in a state where the inflation portion 140 is inflated. The gap portions 143a, 143b, 143c, 143d, and 143e are formed on a surface on the side facing the band 20, and the gap portion 143f is formed on a surface on the side facing the body surface of the wrist W. Each of the gap portions 143a, 143b, 143c, 143d, and 143e is configured to cause the first layer 41 to protrude with a relatively short distance (area) along the traveling direction of the radial artery R. The gap portion 143f is configured to cause the first layer 41 to protrude with a relatively long distance (area) along the traveling direction of the radial artery R.

According to the hemostatic device 100 of first modified exemplary embodiment described above, after the inflation portion 140 is inflated, through the first layer 41 protruding from the gap portions 143a, 143b, 143c, 143d, 143e, and 144f, the gas contained inside the inflation portion 140 can be more efficiently discharged outward from the inflation portion 140 with the lapse of time. In addition, the first layer 41 is configured to protrude from the gap portion 143f on the surface on the side facing the body surface of the wrist W in the inflation portion 40 with the relatively long area along the radial artery R. Accordingly, it is possible to improve the hemostasis effect.

Note that, without being limited to six, the number of gap portions disposed in the single inflation portion 40 can be appropriately changed.

Figure 9:
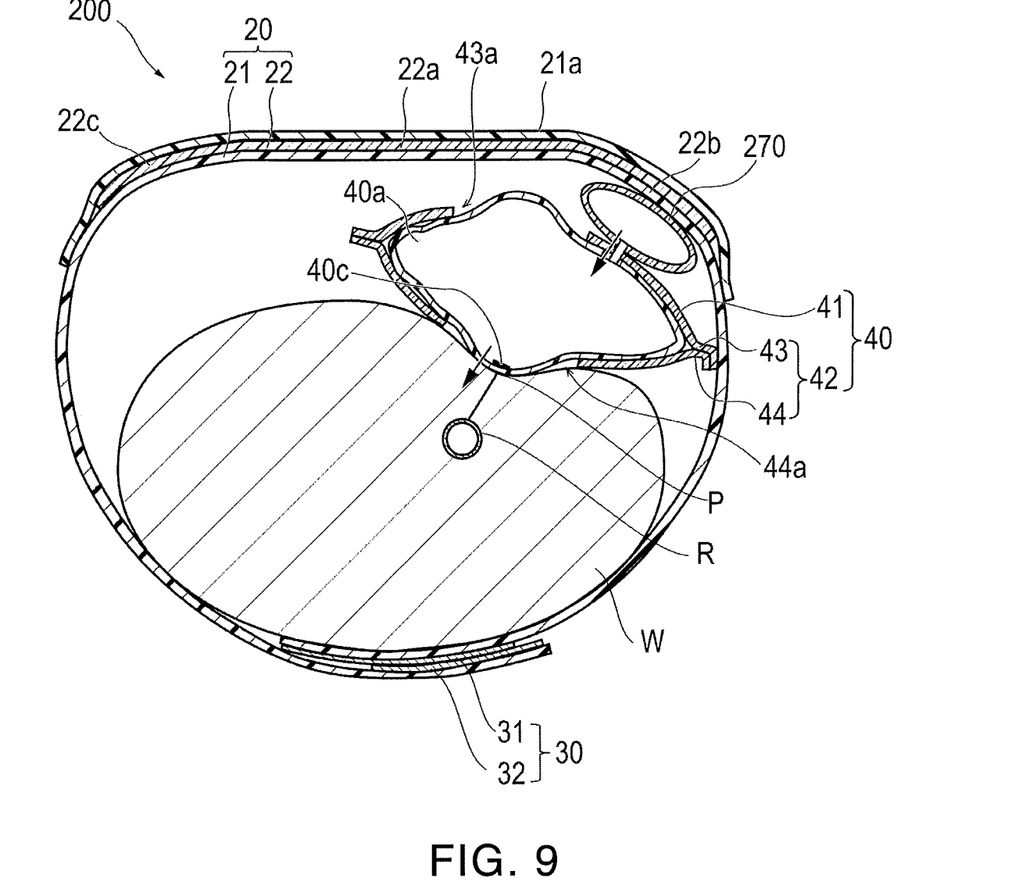
FIG. 9 is a sectional view of a hemostatic device according to a second modified exemplary embodiment.

FIG. 9 is a view corresponding to FIG. 6 of a hemostatic device 200 according to a second modified exemplary embodiment. Hereinafter, the same reference numerals will be given to configurations the same as those according to the above-described embodiment, and description thereof will be omitted.

The hemostatic device 200 according to the second modified exemplary embodiment is different from that according to the above-described exemplary embodiment in that an auxiliary compression portion 270 is provided between the inflation portion 40 and the band 20.

Similar to the inflation portion 40, the auxiliary compression portion 270 is formed in a bag-like shape. The auxiliary compression portion 270 is attached to the first sheet 43 of the inflation portion 40 so that an internal space thereof communicates with the internal space of the inflation portion 40. Therefore, if the gas is injected into the inflation portion 40, the auxiliary compression portion 270 is also inflated. Note that, the auxiliary compression portion 270 may be configured to include a sponge-like substance, an elastic material, an aggregate of fibers such as cotton, or a combination thereof.

According to the hemostatic device 200 of the second modified exemplary embodiment described above, as illustrated by a solid line arrow in FIG. 9, the auxiliary compression portion 270 can adjust the direction of the compressing force applied by the inflation portion 40 so as to be the direction oriented to the puncture site P.

In addition, the auxiliary compression portion 270 is disposed in the first sheet 43. Accordingly, the first layer 41 protruding from the gap portion 43a can increase an area of the exposed portion without coming into contact with the band 20. Therefore, the gas can be more satisfactorily discharged from the exposed portion.

Hitherto, the hemostatic device according to the disclosure herein has been described with reference to the exemplary embodiment and the modified examples. However, without being limited to only the respectively described configurations, the disclosure can be appropriately modified based on the description in the appended claims.

For example, each portion configuring the hemostatic device can be substituted with any optional configuration which can fulfill the same function. In addition, any optional configuration element may be added thereto.

In addition, without being limited to the hemostatic device used by being worn on the wrist, the disclosure herein is also applicable to a hemostatic device used by being worn on a leg.

In addition, according to the above-described exemplary embodiment, at least a portion of the first layer is secured to the inner surface of the second layer. However, the first layer may not be secured to the inner surface of the second layer.

In addition, according to the above-described exemplary embodiment, the first layer protrudes from the gap portion in a state where the inflation portion is inflated. However, a configuration is not limited thereto as long as the first layer is exposed from the gap portion in the state where the inflation portion is inflated. That is, the gap portion may separate and allow the first layer to be exposed without the first layer protruding through the gap portion.

In addition, according to the above-described exemplary embodiment, the gap portion of the second layer is secured so as to be openable when the inflation space inside the inflation portion reaches a predetermined pressure. However, the gap portion of the second layer may not be temporarily secured before the inflation portion is inflated.

In addition, according to the above-described exemplary embodiment, the inflation portion interlocks with the band by means of fusion bonding. However, the inflation portion may not directly interlock with the band. For example, the inflation portion interlocks with the band via a separate member. In this manner, a configuration is adopted so that the inflation portion is not detached from the band.

In addition, according to the above-described exemplary embodiment, the gap portion is formed on both the surface on the side facing the band in the second layer and the surface on the side facing the limb in the second layer. However, the gap portion may be formed in at least one location of the inflation portion.

The detailed description above describes features and aspects of embodiments of a hemostatic device. The disclosure is not limited, however, to the precise embodiments and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A hemostatic device comprising:
    a band adapted to be wrapped around a limb of a patient at a site on the limb where bleeding is to be stopped;
    securing means for securing the band in a wrapped state around the limb; and
    an inflation portion disposed on an inner peripheral surface of the band, and adapted to be inflated by injecting gas;
    wherein the inflation portion has a first layer and a second layer disposed over an outer surface of the first layer;
    wherein the first layer is formed of a material which has a larger gas permeation amount per unit area than a material forming the second layer;
    wherein the second layer has at least one gap portion adapted to expose an outer surface of the first layer outward from the second layer in a state where the inflation portion is inflated; and
    the at least one gap portion including at least one first gap portion formed on a surface of a side of the second layer facing the band when the band is wrapped around the limb of the patient and at least one second gap portion formed on a surface of a side facing the site on the limb where bleeding is to be stopped.

2. The hemostatic device according to claim 1,
wherein the first layer is formed of a thermosetting elastomer; and
wherein the second layer is formed of a thermoplastic resin which has lower gas permeability than the thermosetting elastomer.

3. The hemostatic device according to claim 2,
wherein the band has an interlock region formed of the thermoplastic resin, and with which the inflation portion interlocks; and
wherein the second layer of the inflation portion is fused to the interlock region of the band.

4. The hemostatic device according to claim 1,
wherein at least a portion of the first layer is secured to an inner surface of the second layer.

5. The hemostatic device according to claim 4, wherein a predetermined gap is provided between the first layer and the inner surface of the second layer along a portion of the first layer that is not secured to the inner surface of the second layer.

6. The hemostatic device according to claim 1,
wherein the first layer protrudes from the at least one gap portion in a state where the inflation portion is inflated.

7. The hemostatic device according to claim 1,
wherein the at least one gap portion of the second layer is closed before inflation of the inflation portion and is openable when an inflation space inside the inflation portion reaches a predetermined pressure.

8. The hemostatic device according to claim 1, further comprising a marker for positioning the inflation portion at the site where bleeding is to be stopped.

9. The hemostatic device according to claim 8, wherein the marker is disposed on the inflation portion.

10. The hemostatic device according to claim 1, wherein the at least one gap portion is configured such that, after one hour elapses, an internal pressure of the inflation portion reaches 70%-97% of the internal pressure of the inflation portion at an immediately preceding hour.

11. The hemostatic device according to claim 10, wherein, after four hours elapsed time, the internal pressure of the inflation portion is 30%-80% of an initial internal pressure of the inflation portion.

12. A hemostatic device comprising:
a band adapted to be wrapped around a limb of a patient at a site on the limb where bleeding is to be stopped;
securing means for securing the band in a wrapped state around the limb; and
an inflation portion disposed on an inner peripheral surface of the band, and adapted to be inflated by injecting gas;
wherein the inflation portion has a first layer and a second layer disposed over an outer surface of the first layer; and
wherein the second layer has at least one gap portion adapted to expose an outer surface of the first layer outward from the second layer in a state where the inflation portion is inflated, the at least one gap portion having a closed configuration in a state where the inflation portion is not inflated and the at least one gap portion having an open configuration in a state where the inflation portion is inflated; and
the at least one gap portion includes at least one first gap portion formed on a surface of a side of the second layer facing the band when the band is wrapped around the limb of the patient and at least one second gap portion formed on a surface of a side facing the site on the limb where bleeding is to be stopped.

13. The hemostatic device according to claim 12, wherein, when the at least one gap portion is in the open configuration, the first layer protrudes outwardly through the at least one gap portion.

14. The hemostatic device according to claim 12, wherein the first layer has higher gas permeability than the second layer.

15. The hemostatic device according to claim 14, wherein the first layer has a lower elastic modulus than the second layer.

16. A method of using a hemostatic device, comprising:
wrapping a hemostatic device around a limb of a user and securing a band of the hemostatic device around the limb such that an inflation portion of the hemostatic device overlaps a puncture site on the limb where bleeding is to be stopped, the inflation portion of the hemostatic device having a first layer and a second layer disposed over an outer surface of the first layer; wherein the first layer is formed of a material which has a larger gas permeation amount per unit area than a material forming the second layer; and wherein the second layer has at least one first gap portion formed on a surface of a side of the second layer facing the band and at least one second gap portion formed on a surface of a side facing the puncture site on the limb where bleeding is to be stopped;
injecting an amount of a gaseous substance into the inflation portion such that the inflation portion inflates, thereby opening the at least one first gap portion in the second layer and also opening the at least one second gap portion in the second layer;
exposing a portion of the first layer through the opened at least one first gap portion in the second layer such that a compressing force is applied to the puncture site and also exposing a portion of the first layer through the opened at least one second gap portion in the second layer; and
reducing the compressing force on the puncture site over a predetermined period of time by discharging the gaseous substance through the portion of the first layer exposed through the opened at least one first gap portion.

* * * * *